United States Patent [19]

Ney et al.

[11] Patent Number: 5,215,459
[45] Date of Patent: Jun. 1, 1993

[54] GLASS IONOMER CEMENTS IN A METHOD OF GUIDED TISSUE REGENERATION

[75] Inventors: Thomas Ney, Tübingen; Werner Zöllner, Wörthsee/Steinebach, both of Fed. Rep. of Germany

[73] Assignee: THERA Patent GmbH & Co., KG, Seefeld, Fed. Rep. of Germany

[21] Appl. No.: 735,035

[22] Filed: Jul. 24, 1991

[30] Foreign Application Priority Data

Jul. 26, 1990 [DE] Fed. Rep. of Germany ....... 4023744

[51] Int. Cl.⁵ ................................................. A61C 5/00
[52] U.S. Cl. ........................................ 433/215; 604/49
[58] Field of Search ............... 406/35; 433/215, 217.1, 433/229, 215; 623/11, 16; 106/38

[56] References Cited

U.S. PATENT DOCUMENTS

| | | | |
|---|---|---|---|
| 4,174,334 | 11/1979 | Bertenshaw et al. | 260/29.6 M |
| 4,808,228 | 2/1989 | Randkler | 106/35 |
| 4,927,866 | 5/1990 | Purrmann et al. | 523/115 |
| 5,032,445 | 7/1991 | Scantlebury | 428/158 |

FOREIGN PATENT DOCUMENTS

| | | |
|---|---|---|
| 0331071 | 9/1989 | European Pat. Off. . |
| 2370468 | 6/1978 | France . |
| 2640503 | 6/1990 | France . |
| 2228001 | 8/1990 | United Kingdom . |

*Primary Examiner*—Mark L. Bell
*Assistant Examiner*—Margaret Einsmann
*Attorney, Agent, or Firm*—Birch, Stewart, Kolasch & Birch

[57] ABSTRACT

The invention relates to the use of glass ionomer cements in a method of guided tissue regeneration. In the method, cavities are artificially created by forming glass ionomer cement coverings over bone substance defects, so that osseous regeneration can take place without a growing-in of connective tissue or bacteria colonization occurring in the bone defects.

13 Claims, No Drawings

GLASS IONOMER CEMENTS IN A METHOD OF GUIDED TISSUE REGENERATION

FIELD OF THE INVENTION

The present invention provides a material with which, in a Guided Tissue Regeneration setting a solid covering can easily be created over a bone defect.

BACKGROUND OF THE INVENTION

Often as a result of parodontal infections, a decay of bone substance occurs in the jaw area, as well as a progressive loosening and finally loss of one's affected teeth. Because of bare colla dentis and bare bifurcations (area of root division of the side teeth), the intermediary stages of such infections can lead to painful conditions. Moreover, even after successfully combating parodontal infections, it is usually not possible for affected teeth to again grow in firmly. This is because bone defects in the affected teeth are filled in by connective tissues rather than new bone. This in turn is because, upon concurrent filling of the bone defect, the connective tissue grows considerably faster than bone substance. As such, an osseous regeneration (i.e., "reattachment") rarely occurs in the case of bone defects which result from parodontal infections.

A method of guided tissue regeneration with teeth was introduced to the medical world some time ago. In the method, bone defects in teeth are artificially screened and the cavities formed by the screens are allowed to simply fill up with blood. The screens are intended to prevent the growing-in of connective tissue into the cavities so that bone regeneration can take place in the cavities formed. After removal of the screen, a re-securing of the teeth is thus achievable.

In EP-B 0 171 173 semi-permeable membranes consisting of polytetrafluorethylene (PTFE) are proposed as screen materials. Resorbable tissues for producing such screens are also described in the literature. For example, in a paper given by Dr. Carla Noppe on the occasion of the 1989 Annual Conference of the Deutsche Gesellschaft für Paradontologie on Sep. 29 and 30, 1989 in Aachen, the practical use of semi-permeable PTFE membranes was described. It was pointed out that these membranes have an open microstructure having approximately a 10 μm pore size, into which gingival fibroblasts can migrate and prevent a deep epithelium growth between filter and gingiva. In the clinical trials reported, 40 membranes of various configurations were implanted for 4 to 6 weeks. Even so, the evaluation showed that in the case of 39 operation areas, a deep epithelium growth of 2 to 4 mm did occur under the membranes and large parts of the membranes were colonized by bacteria. Moreover, although the use of such membranes and tissues allowed a certain degree of success to be achieved, their clinical application was extremely difficult. For example, the flexible tissues were secured in situ only with difficulty and moreover, the low biocompatibility of the PTFE membranes necessitated their removal from application sites after only a few weeks. Similarly, deep epithelium growths could not be completely ruled out with the tissues and membranes, and likewise a bacterial colonization could not be prevented therewith.

The concept of GTR can, of course, be applied not only to bone defects in the area of the teeth, but also to other bone defects occurring in the body.

SUMMARY OF THE INVENTION

The invention provides a method for guiding tissue regeneration, wherein a covering is simply and easily created over a bone defect. The coverings possess good biocompatibility and are capable of long-term use in vivo. The coverings use in vivo helps to ensure undisturbed bone growth, without the formation of connective tissue or bacterial colonization in the bone defect.

In the present invention, a guided tissue regeneration is achieved without the use of a semipermeable membrane. Instead, the present invention provides a method of forming a tightly sealed, solid covering over a bone defect, in order to achieve a guided tissue regeneration. The present invention also provides that the coverings consist essentially of a glass ionomer cement(s), since the present inventors have found that the same materials are eminently suited to construct solid coverings over bone defects.

DETAILED DESCRIPTION OF THE INVENTION

The present invention provides for the use of glass ionomer cements in a method of guided tissue regeneration (GTR). More particularly it provides for forming tightly sealed, solid covers over bone substance defects and bone cavities so that GTR can take place.

Because of the plastic deformability of the glass ionomer cements utilized herein, the formation of the present inventive bone defect coverings therewith is greatly facilitated when compared with the use of other materials. Likewise, the adhesion of such glass ionomer cements to bone and tooth substance simplifies the stabilization of such covers in vivo. In this respect, through the use of glass ionomer cement coverings, it is possible for the soft tissue lying over them to knit together and stabilize in a manner which is problem-free. Likewise, due to their good tissue compatibility, the covers can remain in situ for several months without causing problems.

It has been found in clinical studies that following removal of the present inventive coverings after approximately three months in situ, new tooth-securing apparatuses have been formed physiologically, and previous loosened teeth containing bone defects have been firmly secured and retained in treated patients' jaws. The results achieved with the coverings of the present invention were so good in fact, that restitutio ad integrum practically occurred in many cases. Additionally, a growing-in of connective tissues and a colonization by bacteria were not even observed in the treated bone defects.

Of the glass ionomer cements which are suitable for use in the present invention, those which are felt most preferable to use comprise the following ingredients:
 (a) an aluminum fluorosilicate glass,
 (b) at least one polymeric polyacid with an average molecular weight >500,
 (c) water, and
 (d) optionally a chelate-forming agent.

As constituent (a), the calcium aluminum fluorosilicate glasses described in DE-A-20 61 513 and in EP-A-0 023 013 and the strontium aluminum fluorosilicate glasses described in EP-A-0 241 277 can be used. In addition to oxygen, the aluminum fluorosilicate glass powders used in the present invention preferably comprise:

| Constituent | Calculated as | % by weight |
|---|---|---|
| Si | $SiO_2$ | 20–60 |
| Al | $Al_2O_3$ | 10–50 |
| Ca | CaO | 0–40 |
| Sr | SrO | 0–40 |
| F | F | 1–40 |
| Na | $Na_2O$ | 0–10 |
| P | $P_2O_5$ | 0–10 | with at least 1% by weight of CaO and/or SrO being present; and in addition a total of 0 to 20% by weight, calculated as oxides, of B, Bi, Zn, Mg, Sn, Ti, Zr, La or other trivalent lanthanoids, K, W, Ge, as well as further additives which do not impair the glasses' properties and are physiologically acceptable. The glass can be made X-ray visible if desired by adding 10 to 20% by weight of $La_2O_3$.

More preferably, the powder particles of glass comprise:

| | | |
|---|---|---|
| Si as $SiO_2$ | 25–50% | by weight |
| Al as $Al_2O_3$ | 10–40% | by weight |
| Ca as CaO | 0–35% | by weight |
| Sr as SrO | 0–35% | by weight |
| F | 5–30% | by weight |
| Na as $Na_2O$ | 0–8% | by weight |
| P as $P_2O_5$ | 1–10% | by weight | with at least 10% by weight of Ca (calculated as CaO) and/or Sr (calculated as SrO) being present; and 0 to 10% by weight of $B_2O_3$, $Bi_2O_3$, ZnO, MgO, $SnO_2$, $TiO_2$, $ZrO_2$, $La_2O_3$ or other oxides of trivalent lanthanoids, $K_2O$, $WO_3$, $GeO_2$, as well as further additives which do not impair the glass properties and are physiologically acceptable.

Most preferably, the powder particles of glass comprise:

| | | |
|---|---|---|
| Si as $SiO_2$ | 25–45% | by weight |
| Al as $Al_2O_3$ | 20–40% | by weight |
| Ca as CaO | 10–30% | by weight |
| F | 10–30% | by weight |
| Na as $Na_2O$ | 1–8% | by weight |
| P as $P_2O_5$ | 1–10% | by weight |

The glass powders used according to the present invention have an average particle size (weighted average) of at least 1 μm and preferably at least 3 μm. The average particle size (weighted average) is 1–20 μm, preferably 3–15 μm and most preferably 3–10 μm. The particles have a maximum particle size of 150 μm, preferably 100 μm, most preferably 60 μm.

The powders used in the present invention may be optionally subjected to a surface treatment as per European Patent 0 023 013. To this end, the glass powders are treated on their surface with acid, preferably at room temperature. Acid-group-containing substances are used, e.g., hydrochloric acid, sulfuric acid, nitric acid, acetic acid, propionic acid or perchloric acid, which form soluble calcium salts or strontium salts. The acids are used in a concentration of 0.01 to 10% by weight, preferably 0.05 to 3% by weight. After the corresponding reaction time, the powders are separated from the solution and thoroughly washed so that after washing, practically no soluble calcium or strontium salts are located on the surface of the powder particles.

The polymeric polyacids which are used as constituent (b) in the present inventive compositions can, for example, be polycarboxylic acids already used in the preparation of glass ionomer cement powders (e.g., polymaleic acid, polyacrylic acid, polyitaconic acid and mixtures thereof or copolymers thereof, particularly the maleic acid/acrylic acid copolymers and/or acrylic acid/itaconic acid copolymers known from EP-A-O 024 056). The average molecular weight of the polycarboxylic acids used in the present invention is more than 500. An average molecular weight of 1,000 to 20,000 is thought to be preferable, and from 3,000 to 10,000 is thought to be especially preferable. The concentration of the polyacid component (b) utilized in the glass ionomer cement is preferably 5 to 50% by weight, relative to the amount of constituent (a).

Also suitable as polymeric polyacids in the present invention are polyphosphonic acids (e.g., polyvinylphosphonic acids and the like). These polyphosphonic acids can completely or partially replace the above described polycarboxylic acids in the coverings of the present invention.

As the constituent (c), water is used in the glass ionomer cement compositions in quantities of 5 to 70% by weight, preferably 15 to 40% by weight, relative to the overall weight of the cement compositions.

A chelate-forming agent, such as is described in DE-A-23 19 715, can be contained as constituent (d) in the preferable glass ionomer cement compositions of the present invention. Tartaric acid is preferably used as the chelate-former. The chelate-formers can be used in concentrations of 0.1 to 10, preferably 3 to 8% by weight, relative to the overall weight of the cement compositions.

In order to obtain a glass ionomer cement having high storage stability (i.e., prior to its use in preparing one of the present inventive coverings), it is thought advisable to add preservatives thereto (e.g., benzoic acid or the like). The preservative(s) are preferably added to a dry polyacid component of the compositions. However, the same is not mandatory.

Additives for regulating the compositions' viscosity (e.g., pyrogenic silicic acid or the like) may be used if desired. Suitable concentrations of such ingredients are 0.1 to 10% by weight, preferably 1 to 5% by weight, relative to the overall weight of the cement compositions.

The glass ionomer cements of the present invention can, moreover, contain chemotherapeutics as per DE 40 19 617. Suitable chemotherapeutics are, for example, cytostatics (such as methotrexate, vincristine, cisplatin, cyclophosphamide or the like) antibiotics such as gyrase inhibitors (e.g., ciprofloxacin, ofloxacin, norfloxacin and salts thereof) as well as aminoglycoside antibiotics, particularly the class of lincomycins. Especially preferred are clindamycin and lincomycin as well as their salts and derivatives. The combination of several active substances can also be suitable in order to optimally treat special indication areas. With regard to suitable gyrase inhibitors, reference is made to W. Still, FAC volume 6–10, 1987, pages 1575–1583. All compounds described therein are considered useful in the present inventive coverings and methods.

The concentration of the chemotherapeutics which are present should be at a maximum of 10% by weight, preferably a maximum of 3% of weight, relative to the overall weight of the glass ionomer cement and the added chemotherapeutics. Especially preferred is an amount in the range of 0.01 to 3% by weight.

The glass ionomer cement is preferably presented in a capsule which contains a powder and a fluid which are initially separated. Thereafter the powder and liquid are brought together, and a glass ionomer cement composition is prepared therewith by mechanical mixing with a usual shaker device.

An application capsule according to EP-A-O 157 121 is preferably used.

It is important that the starting components (powder and liquid) are provided under sterile conditions. The sterilization can take place by heat treatment, sterile filtration (liquid) or particularly by gamma radiation.

The constituents of a glass ionomer cements of the present invention comprise:
(a) a glass powder,
(b) a polymeric polyacid,
(c) water, and
(d) a chelating agent;
these ingredients can be divided in various ways between a powder and liquid portion:

| Powder (or solid) | Liquid (or paste) |
| --- | --- |
| (a) | (b) + (c) + (d) |
| (a) + (b) | (c) + (d) |
| (a) + (b) + (d) | (c) |

Paste/paste divisions are also possible, in which combinations with, e.g., component (c) would be possible.

The glass ionomer cements according to the invention are applied to cure bone substance defects as well as bone continuity interruptions. In particular, bone defects in the jaw area resulting from parodontal diseases can be regenerated by the application of glass ionomer cements in coverings according to the present invention. Exemplary of the bone defects which can be treated according to the present invention are parodontal vertical decay, parodontal lateral decay and parodontal furcation attack, the methods of the present invention can also be used in the treatment of atrophied alveolar process in dental implantology. Likewise, cystic bone defects in the skeleton system can be osseously regenerated by application of a glass ionomer cement cover such as proved for in the present invention.

EXAMPLE

A conventional glass ionomer cement is used:
Powder: calcium aluminum fluorosilicate glass, average particle size approximately 8 μm.
Liquid: solution of 39 g of a copolymer (1:1) comprising acrylic acid and maleic acid and 10 g tartaric acid in 51 g distilled water.

A film sachet, which is attached to an application capsule as per EP-B 0 157 121, is filled with 340 mg of the liquid. The main chamber of the application capsule is filled with 860 mg of the cement powder. The capsule is blistered and sterilized with gamma rays.

An elderly patient has a furcation attack on the first molar of the lower jaw. This means that the tooth support apparatus is atrophied at the root furcations. The defect is continuous through the furcation in the buccolingual direction. This is a class III furcation attack. A parodontal surgical operation follows. The mucous membrane is folded back from the tooth and alveolar process. The tooth is cleaned, curetted and scaled. The bone substance loss as well as the loss of the tooth support tissue becomes clear. Now, using the sterile glass ionomer cement, a cover is constructed for the therapy of this substance loss in situ. The cement capsule is mixed for 10 seconds in a usual mixer. The cement taken is shaped in the form of a tent-roof from the bone to the tooth. The glass ionomer cement binds not only to the bone but also to the tooth substance. Thus, an impermeable seal is provided not only to the tooth but also to the alveolar bone. The growing-in of the connective tissue and epithelium is hindered by the very tight seal. This modelling takes place both on the lingual and on the buccal tooth face. Between the two "bone covers", a cavity remains around the root furcation. This cavity fills up intra operationem with blood. Progenitor cells orient themselves from the bone marrow as well as from the subepithelial connective tissue of the gingiva, which cells rebuild the parodontal ligament to the formerly bare root faces in this cavity. After successful modelling and checking of the operation result, the mucous membrane is sown together again over the defect. The cover remains approximately three months in situ. If there are no problems, the cover can remain even longer in situ. After approximately three months, a new tooth support apparatus has formed at the root furcations. Thus, the tooth can be preserved.

With conventional parodontal-therapeutic possibilities, a furcation attack leads to the extraction of the affected tooth. With the help of the construction of a corresponding bone cover made of a glass ionomer cement it is possible, as shown here, to treat the parodontal vertical and lateral decay, as well as the furcation attack. As such, extraction of the tooth is no longer necessary.

Each of the cited patents, references and/or publications referred to herein above, are expressly incorporated herein by reference in their entirety.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A method of guiding tissue regeneration, comprising:
    forming a tightly sealed, solid covering over a bone defect in vivo, wherein a cavity is formed between the covering and the bone defect, and wherein the covering consists of a glass ionomer cement.

2. A method of guiding tissue regeneration as recited in claim 1, wherein said bone defect occurs in the teeth or jaw of a patient.

3. A method of guiding tissue regeneration as recited in claim 1, wherein the glass ionomer cement comprises:
    (a) an aluminum fluorosilicate glass,
    (b) at least one polyacid with a molecular weight of >500, and
    (c) water.

4. A method of guiding tissue regeneration as recited in claim 1, wherein the glass ionomer cement comprises:
    (a) an aluminum fluorosilicate glass,
    (b) at least one polyacid with a molecular weight of >500,
    (c) water, and
    (d) a chelating agent.

5. A method of guiding tissue regeneration as recited in claim 1, wherein the glass ionomer cement comprises:
    (a) an aluminum fluorosilicate glass, (b) at least one polyacid with a molecular weight of >500,
(c) water, and
(d) at least one chemotherapeutic.

6. A method of guiding tissue regeneration as recited in claim 1, wherein the glass ionomer cement comprises:
(a) an aluminum fluorosilicate glass,
(b) at least one polyacid with a molecular weight of >500,
(c) water,
(d) a chelating agent, and
(e) at least one chemotherapeutic.

7. A method of guiding, tissue regeneration as recited in claim 1, 3, 4, 5, or 6 wherein the glass ionomer cement is prepared by mixing together at least two spatially separate partial compositions.

8. A method of guiding tissue regeneration as recited in claim 7, wherein at least one of the partial compositions is present in a solid or powder form and at least one of the other partial compositions is present in a liquid or paste form.

9. A method of guiding tissue regeneration as recited in claim 8, wherein:
the aluminum fluorosilicate glass is contained in a partial composition having a solid or powder form; and
the polyacid and the water are contained in a partial composition having a liquid or paste form.

10. A method of guiding tissue regeneration as recited in claim 9, wherein:
a chelating agent is present in the glass ionomer cement composition and is contained in the partial composition having a liquid or paste form.

11. A method of guiding tissue regeneration as recited in claim 8, wherein:
the aluminum fluorosilicate glass and the polyacid are contained in a partial composition having a solid or powder form; and
the water is contained in a partial composition having a liquid or paste form.

12. A method of guiding tissue regeneration as recited in claim 11, wherein:
a chelating agent is present in the glass ionomer cement compositions and is contained in the partial composition having a solid or powder form.

13. A method of guiding tissue regeneration as recited in claim 11, wherein:
a chelating agent is present in the glass ionomer cement compositions and is contained in the partial composition having a liquid or paste form.

* * * * *